(12) United States Patent
Matuszewski et al.

(10) Patent No.: US 7,858,924 B2
(45) Date of Patent: Dec. 28, 2010

(54) DEVICE FOR USE IN NORMALIZING READINGS ON A TESTING MACHINE

(75) Inventors: Paul A. Matuszewski, Wauconda, IL (US); Omar S. Khalil, Chicago, IL (US); Kurt M. Klosterman, Gurnee, IL (US); James L. Dempski, Green Oaks, IL (US); Jose Pioquinto, Round Lake, IL (US)

(73) Assignee: Abbott Laboratories, Inc., Abbott Park, IL (US)

( * ) Notice: Subject to any disclaimer, the term of this patent is extended or adjusted under 35 U.S.C. 154(b) by 1050 days.

(21) Appl. No.: 11/637,314

(22) Filed: Dec. 12, 2006

(65) Prior Publication Data

US 2008/0135743 A1    Jun. 12, 2008

(51) Int. Cl.
*G01D 18/00*   (2006.01)
*G12B 13/00*   (2006.01)

(52) U.S. Cl. ............................. 250/252.1; 250/361 R; 250/362

(58) Field of Classification Search ............. 250/252.1, 250/361 R, 362
See application file for complete search history.

(56) References Cited

U.S. PATENT DOCUMENTS 4,652,533 A    3/1987   Jolley
5,006,309 A    4/1991   Khalil et al.
5,089,424 A    2/1992   Khalil et al.
5,198,368 A    3/1993   Khalil et al.
5,244,630 A    9/1993   Khalil et al.
RE34,405 E    10/1993   Gould et al.
5,283,178 A    2/1994   Kessler et al.
5,441,894 A    8/1995   Coleman et al.
5,468,649 A   11/1995   Shah et al.

*Primary Examiner*—David P Porta
*Assistant Examiner*—Mark R Gaworecki
(74) *Attorney, Agent, or Firm*—David L. Weinstein

(57) ABSTRACT

An optic module verification device for normalizing between X photon counters, including a verification tray with X verification wells and a modular photon emitter in each verification well. Each photon emitter includes a spring, a Beta source disk, a scintillator disk adjacent the Beta source disk, and a neutral density filter over the scintillator disk, all of which are encapsulated in a cylindrical chamber with the filter adjacent an opening on one end of the chamber and the spring biasing the Beta source disk and the scintillator disk toward the opening. The device is periodically used for normalization, and may be updated when emitted photons fall below a desired level by replacing the scintillator disk and then determining a new normalized reference values for each photon emitter.

13 Claims, 6 Drawing Sheets

DEVICE FOR USE IN NORMALIZING READINGS ON A TESTING MACHINE

CROSS REFERENCE TO RELATED APPLICATION(S)

Not applicable.

STATEMENT REGARDING FEDERALLY SPONSORED RESEARCH OR DEVELOPMENT

Not applicable.

REFERENCE TO A MICROFICHE APPENDIX

Not applicable.

TECHNICAL FIELD

The present invention relates to normalizing readings on testing machines, and more particular to normalizing photon count readings on testing machines having more than one photon counter.

BACKGROUND OF THE INVENTION AND TECHNICAL PROBLEMS POSED BY THE PRIOR ART

Testing of biological samples is often carried out using, for example, wet chemistry, in conjunction with automatic testing machines. In some such tests, samples are dispensed in reaction trays having a plurality of wells for handling a plurality of samples, with the analysis of the different samples often involving counting photons emitted from the samples. There is no known single photon counting standard, however, and, therefore, it is only possible to obtain relative relationships between single photon sources and photon detectors (photon counters).

Further, there is an intrinsic variability among photomultiplier tubes used to count photons, which variability requires a normalization method to obtain similar count values among different photon counters, such as are typically encountered in testing machines (a plurality of photon counters facilitates higher volume testing). In such cases, for example with the ABBOTT PRISM™ System available from Abbott Laboratories, Inc. of 100 Abbott Park Road, Abbott Park, Ill. 60064, the testing machine may have a plurality of different tracks for different types of tests, with each track having two photon counters, which are used in conjunction with trays having a plurality of rows of wells, with each row having two wells (e.g., two columns of wells in eight rows). In use, a tray is advanced through the testing machine row by row, with one photon counter counting photons emitted from each well of one column of wells and the second photon counter counting photons emitted from each well of the other (adjacent) column of wells.

Given the intrinsic variability and extremely sensitive nature of photon counters, however, it is essentially impossible to expect that each of the photon counters will be identical, or will obtain identical results even under identical conditions (which can never be achieved in any event). Therefore, it has been necessary to normalize the readings obtained by different photon counters, that is, to determine a factor of difference between the photon counters, which may be used to obtain comparable results among a plurality of photon counters. For example, in a simplified example, if a known source is read, and one photon counter is found to return readings that are 10% higher than the known source, and the other photon counter is found to return readings that match what would be expected from the known source, readings taken during testing by the former photon counter would be reduced to take into account the 10% overcount, thereby giving test results that are therefore more reliable. Of course, accurate test results are particularly critical in many such biological testing situations, because incorrect results are not merely testing failures, but may also result in a misdiagnosis of an individual's condition and subsequent improper treatment of a patient.

In order to determine normalization values among photon counters of a testing machine, optic module verification tools (OMVT) have heretofore been used. Such devices are essentially duplicates of reaction trays, including at least one well in each column (i.e., associated with each photon counter) having a known photon emitter.

The well of a tray 10 including such a prior art photon emitter in one of the wells of the tray is illustrated in FIG. 1. Specifically, the photon emitter 20 is disposed beneath a tray well 22, and includes an optic standard 26 contained within a capsule 28, both of which rest on a cap 30. Suitably secured over the optic standard 26 is a filter glass 34, and a foam support 36 is provided at the bottom of the tray 22 to assist in locating the filter glass 34 at the desired position adjacent the bottom of the tray well 22. The optic standard 26 is carbon-14 ($C_{14}$) mixed with a suitable epoxy resin as a soup or slurry, which is then cast in the desired plug shape.

For normalization, the photon emission of each photon emitter is first measured according to a standard. For example, normalization trays have been measured at a central location where such standardized measurements can take place, with each photon emitter assigned the measured photon count. Such normalization trays have then been distributed for use with testing machines, with one normalization tray provided at each geographic location where a testing machine is found.

At each testing machine, the normalization tray is run through the machine one or more times in order to obtain a photon count by each photon counter from the photon emitter associated therewith. The photons counted at the test machine by each photon counter are then been compared to the assigned measured photon count as previously determined for each photon emitter, with those values used to normalize the results obtained by the different photon counters, when photons emitted from test specimens are subsequently counted.

Unfortunately, while the photon emitter such as described above might be thought to be subject to little decay, because it is based on $C_{14}$ having a long half-life (5568 years), experience has shown that the photons emitted by such emitters in fact may decay relatively quickly, so that the quantity of emitted photons may fall below a desired minimum level in as short a period of time as a few months. In that case, a new optic module verification device (normalization tray) can be obtained from the central location (or the old one must be essentially completely remanufactured with a new photon emitter) with normalization values obtained against the standard. Alternatively, the device can continue to be used after being re-measured according to the standard, but with photon emissions that are below the preferred minimum level for reliable normalization of the test machine. Neither option is preferred for both cost and operational reasons.

The present invention is directed toward overcoming one or more of the problems set forth above.

SUMMARY OF THE INVENTION

In one aspect of the present invention, an optic module verification device is provided for use for periodic normalization of a testing machine used to test samples in wells of reaction trays, where the testing machine includes X photon counters, which each count photons emitted from different tray wells, where X is an integer greater than 1. The verification device includes a verification tray defining at least X verification wells and a photon emitter in each verification well. The verification wells are located so as to each be associated with a different one of the photon counters when used in the testing machine. Each photon emitter includes a $C_{14}$ source, a scintillator adjacent the $C_{14}$ source, and a filter over the scintillator, wherein each photon emitter has a determined initial base value for emitted photons, and each photon emitter is positioned in its verification well to emit photons through the filter to the associated photon counter when used in the testing machine.

In one embodiment of this aspect of the present invention, the filter is a neutral density glass filter.

In another embodiment of this aspect of the present invention, the scintillator is a plastic element with opposite generally flat surfaces. In a further embodiment, one surface of the scintillator is abraded, e.g., roughened, to minimize internal reflectivity.

In still another embodiment of this aspect of the present invention, the verification device includes an open bottom tray in each of the verification wells, and the photon emitters are positioned beneath the bottom of the tray with the filter adjacent the opening in the bottom of the tray. In a further embodiment, a capsule is removably securable to a cap to define a space therebetween for enclosing the photon emitter, the capsule including a shoulder surrounding an opening against which the filter is secured, and a spring is positioned between the cap and the $C_{14}$ source to bias the $C_{14}$ source and the scintillator against the filter. In still a further embodiment, the capsule shoulder is aligned with the opening in the bottom of the tray.

In yet another embodiment of this aspect of the present invention, additional wells in the verification device are closed to prevent emission of photons, with the additional wells each being positioned so as to be associated with one of the photon counters.

In another embodiment of this aspect of the present invention, the testing machine is adapted to count photons of a selected wavelength of light based on designed wet chemistry for a test specimen, and the scintillator mimics the selected wavelength of light.

In still another embodiment of this aspect of the present invention, the $C_{14}$ source comprises a steel disk having a surface adjacent the scintillator, the surface coated with $C_{14}$ having about five (5) micro-curies of activity.

In yet another embodiment of this aspect of the present invention, a mylar coating overlies the $C_{14}$ coating on the surface of the steel disk.

In another aspect of the present invention, a modular photon emitter is provided, the emitter including a spring, a disk including a Beta source, a plastic scintillator disk adjacent the Beta source, a neutral density filter over the scintillator disk, and a bottom cap and a capsule securable together to define a cylindrical chamber with an opening at one end of the capsule. The spring, the disk including a Beta source, the plastic scintillator disk, and the filter are encapsulated in the cylindrical chamber with the filter adjacent the aforementioned opening at one end of the capsule and the spring biasing the disk including a Beta source and the plastic scintillator disk toward the opening.

In one embodiment of this aspect of the present invention, the surface of the scintillator disk adjacent the Beta source disk is roughened.

In another embodiment of this aspect of the present invention, the Beta source is $C_{14}$.

In still another embodiment of this aspect of the present invention, the capsule includes an annular face surrounding the opening, and the filter is secured against the annular face.

In yet another embodiment of this aspect of the present invention, the bottom cap and the capsule include mating threads for releasably securing the bottom cap and the capsule together.

In still another aspect of the present invention, a method is provided for periodically normalizing two photon counters of a testing machine used to test samples in wells of reaction trays by counting photons emitted from the wells of the reaction trays. The method includes the step of (a) initially providing a verification device having two photon emitters, each photon emitter including a $C_{14}$ source, a scintillator adjacent the $C_{14}$ source, and a filter over the scintillator. Then, in step (b) normalized reference values for each photon emitter are determined, in step (c) photons emitted from the photon emitters of the verification device are counted on the testing machine, wherein one of the photon counters counts the photons emitted from one of the photon emitters and the other photon counter counts the photons emitted from the other photon emitter, in step (d) normalization values for the photon counters are determined based on the normalized reference values and the photons emitted from the photon emitters counted by the photon counters, in step (e) samples are tested in wells of the reaction tray by counting photons using the two photon counters, and in step (f) the values of photons counted from the samples are normalized using the normalization values. Then, in step (g), steps (e) and (f) are repeated to test a plurality of reaction trays having wells with samples therein, and in step (h), steps (c) and (d) are periodically repeated. When the counted photons in step (c) fall below a predetermined value, the verification device is updated by replacing the scintillator of each photon emitter, and repeating steps (b) through (h).

In one embodiment of this aspect of the present invention, the scintillators are chosen so that the photon emitters each have an initial reference value for emitted photons as determined in step (b) within a selected range, with the predetermined value being the lower end of the selected range.

DETAILED DESCRIPTION OF THE INVENTION

A normalization tray 100 with photon emitters 102 for use in normalizing readings on a testing machine or instrument 104 (see FIG. 6) is illustrated in FIGS. 2-5.

Figure 3:
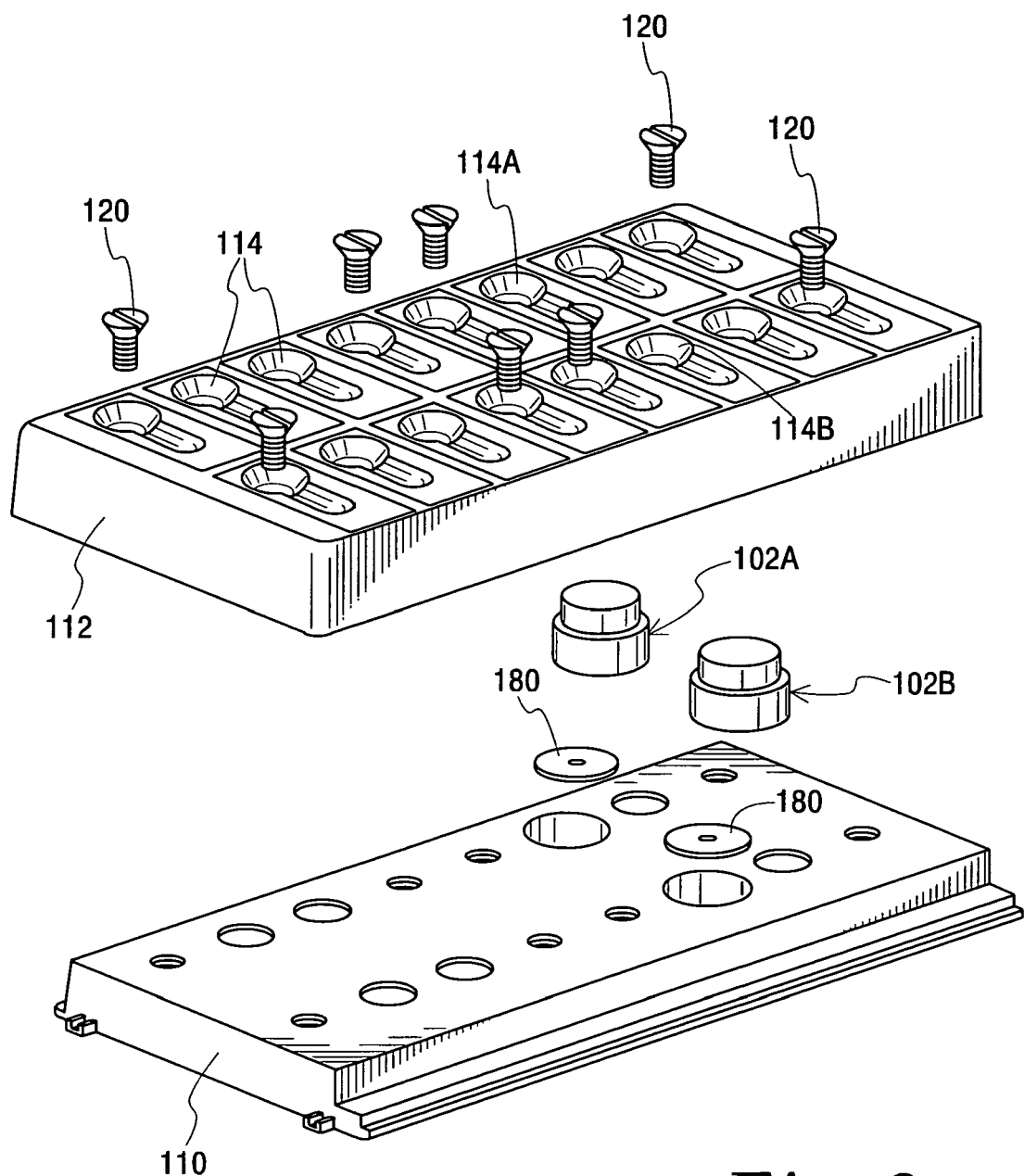
FIG. 3 is an exploded view of a normalization tray according to the present invention.

The tray 100 includes a base 110 beneath a reaction tray 112 defining a plurality of wells 114, specifically sixteen wells 114 in two columns of wells having eight rows (see FIG. 3). It should be appreciated that not all of the wells are used with this normalization tray 100, but that such a configuration is advantageously used to match the configuration of trays used in testing so that the normalization tray 100 can be conveniently handled in the testing machine 104. Thus, screw plugs 120 can be advantageously secured in those wells 114 that are not actually used for normalization (e.g., by securing those plugs in threaded inserts 122 in the tray base 110 as shown in FIG. 4).

Figure 4:
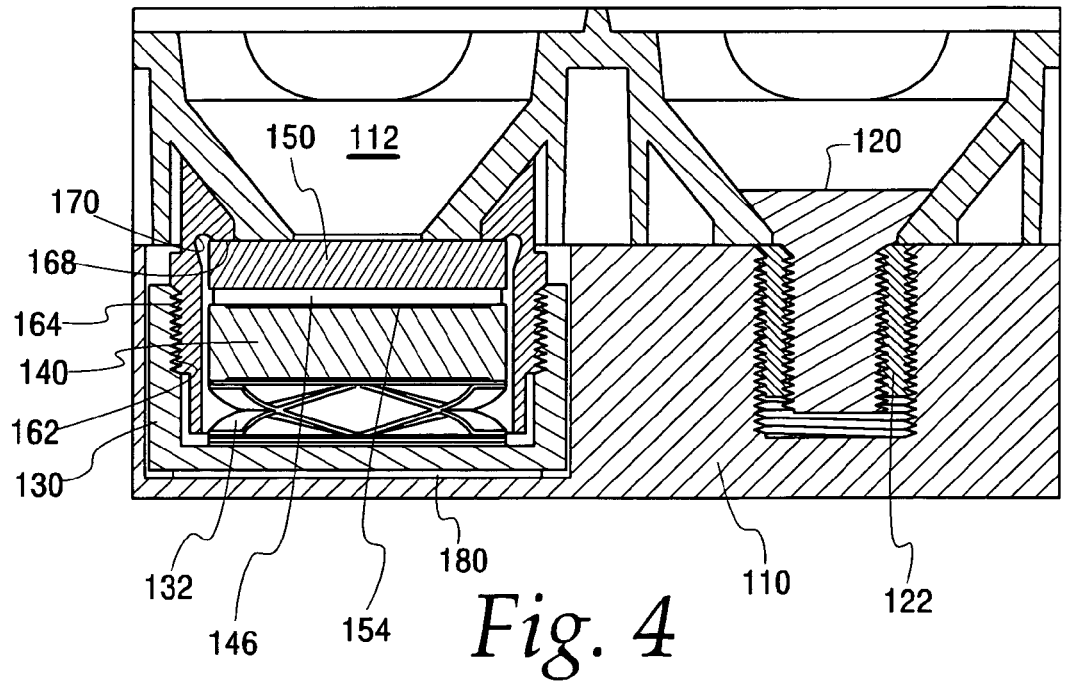
FIG. 4 is a cross-sectional view of two wells of a normalization tray according to the present invention, with one well including a photon emitter.
Figure 2:
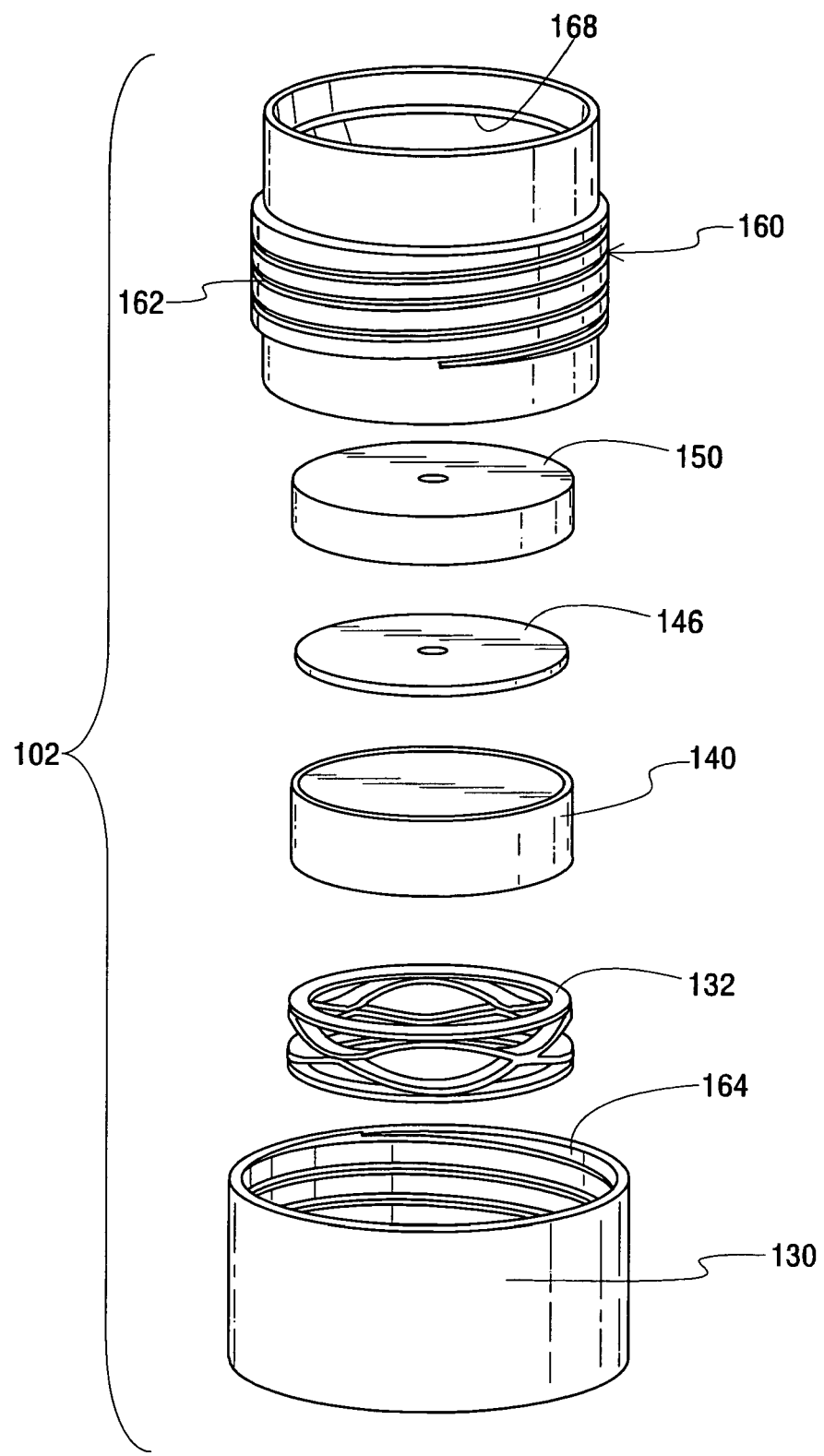
FIG. 2 is an exploded view of a photon emitter according to the present invention.

A photon emitter 102 according to the present invention is illustrated in FIGS. 2 and 4. The photon emitter 102 includes a stainless steel knurled bottom cap 130 with a suitable spring member 132 (e.g., a wave spring such as illustrated) disposed therein. Supported above the spring member 132 is a $C_{14}$ source 140, a plastic scintillator disk 146, and a suitable filter glass 150.

The $C_{14}$ source 140 can advantageously be a steel disk with a $C_{14}$ plating on the top surface of the disk and a mylar coating thereon, with sufficient $C_{14}$ applied to provide about 5 microcuries of activity.

The scintillator disk 146 absorbs energy emitted by the $C_{14}$ source 140 and, in response, fluoresces photons at a characteristic wavelength. The material of the plastic scintillator disk 146 can thus be selected so as to generate photons at the wavelength to be detected by the testing machine 104. For example, if the testing machine 104 operates to count photons in a blue wavelength (e.g., about 420 nanometers) to determine wet chemistry test results for biological samples, a plastic scintillator disk 146 that will emit photons at about 420 nanometers (such as a polyvinyl toluene disk) can advantageously be chosen for inclusion in the photon emitter 102. For example, an Eljen-212 plastic scintillator disk (having a polyvinyltoluene polymer base, and available from Eljen Technology, 300 Crane Street, Sweetwater, Tex. 79556) having a half inch diameter and 0.020 inch thickness can be used.

Further, it has been found that abrading, e.g., roughening or sanding, at least one flat surface of the scintillator disk 146 (so as to not have the smoother surface generally produced by molding of such disks) will advantageously minimize internal reflectivity of the plastic scintillator disk 146. For example, sanding of the material of the plastic scintillator disk can be advantageously performed using a random-orbital sander and 400 grit sandpaper, with the sanding (wet or dry) performed to yield a uniform scoring/dullness of the cast sheet of scintillation material. The operation is done to yield a level of scoring/dullness involving only the briefest exposure to the sander, with the sanding removing less than 5% of the original thickness of the cast sheet of scintillation material. Glass-bead blasting is another method that has also been found to acceptably mar the plastic scintillator disk 146. Preferably, only the side of the plastic scintillator disk 146 that faces the Beta source ($C_{14}$ source 140) is sanded, with the other side of the plastic scintillator disk 146 being left alone.

The filter glass 150 serves to knock back some of the light, and thereby helps the photon counters (photodiscriminators) better count single photon events. For example, a Schott NG-5 neutral grey glass density filter can be advantageously used (e.g., a filter having a half inch diameter and thickness of about 0.079 inch).

A cylindrical stainless steel capsule 160 is configured so as to encapsulate the spring 132, the $C_{14}$ source 140, the plastic scintillator disk 146, and the filter glass 150. As best shown in FIG. 2, the capsule 160 includes an outer threaded portion 162 so that it can be secured to the bottom cap 130 by screwing into an inner thread 164 of the bottom cap 130. Further, the upper end of the capsule 160 is tapered so as to generally match the underside of the tapered well 114 of the reaction tray 112, and the upper end of the capsule 160 further includes a downwardly facing annular surface 168 adapted to be engaged against the upper face of the filter glass 150.

The filter glass 150 can be suitably secured to the capsule 160, by means of gluing, by means of a low bloom "super glue" (e.g., cyanoacrylate glue that does not evaporate out onto the surrounding surfaces). A relief groove 170 around the capsule's annular surface 168 can be advantageously provided for excess glue from that attachment, helping to also ensure that glue does not disadvantageously leak onto the top of the filter glass 150, through which photons are intended to pass.

It should be appreciated, therefore, that the photon emitters 102 will be reliably configured with the plastic scintillator disk 146 and the $C_{14}$ source 140 pressed up against the underside of the filter glass 150 by the spring 132.

Foam member(s) 180 or other suitable spring-like member(s) can also be advantageously provided beneath the photon emitter(s) 102 near the bottom of the tray base 110 to ensure that the photon emitter(s) 102 are positioned precisely as desired, with the filter glass 150 against the bottom of the well 114 defining portion of the reaction tray 112.

Figure 5:
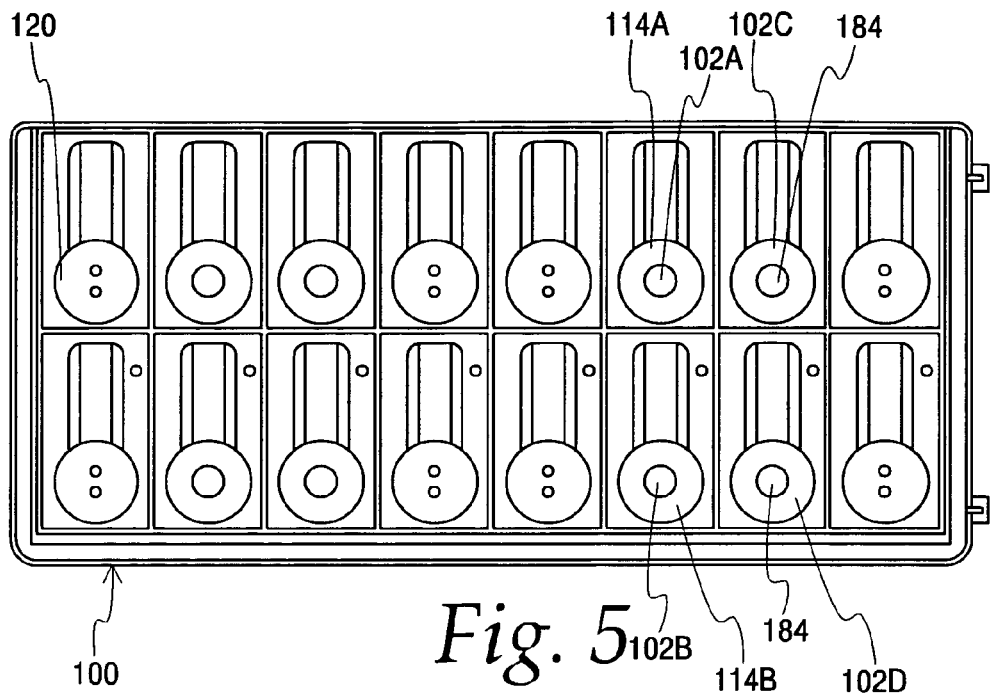
FIG. 5 is a plan view of the normalization tray according to the present invention.

As illustrated in FIG. 5, the tray 100 can include a row with two wells 114A, 114B with photon emitters 102A, 102B. Adjacent wells 114C, 114D can be provided with black pieces of foam material 184 to block the openings at the bottom of the wells 114C, 114D to provide wells where no photons will be present (and thereby provide a check when normalizing the photon counters).

Figure 6:
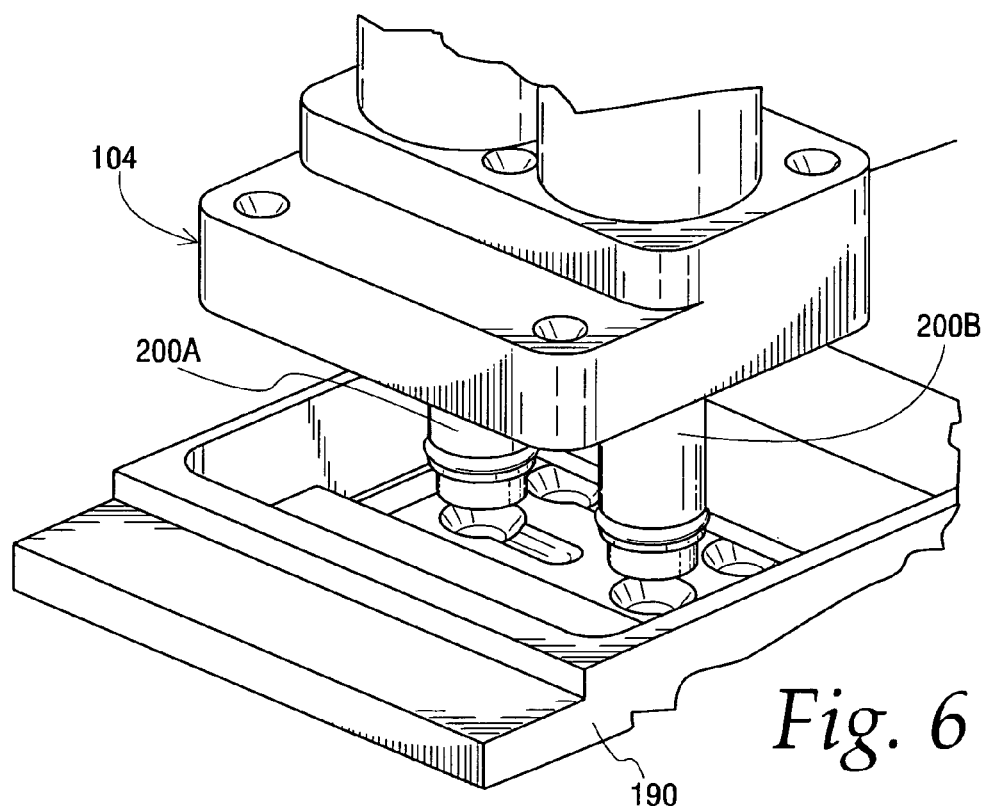
FIG. 6 is a perspective view illustrating use of the normalization tray according to the present invention with a testing machine having two photon counters.

FIG. 6 illustrates how to use the tray 100 of the present invention to normalize the photon counters of a testing machine or analyzer 104, that is, as would occur when testing samples (in which test results can be determined by counting the photons generated by wet chemistry on, e.g., biological samples in different wells of a similar tray, with the wet chemistry of the sample generating light via chemical luminescence, wherein the quantity of light emitted is proportional to the chemical reactivity). The tray 100 is moved through a track 190 of the analyzer 104 so as to index the tray wells 114 beneath photodiscriminators or photon counters 200A, 200B of the analyzer 104. Photon counts are recorded for at least wells 114A, 114B, and preferably also wells 114C, 114D (to verify that essentially no photons are counted at wells 114C, 114D). (A suitable shroud surrounding the wells 114 and photon counters 200A, 200B can be provided to prevent environmental photons from affecting the count; however, that shroud has been omitted from the figures for the sake of simplification.) In this manner (as discussed below and essentially as previously accomplished), the readings determined by the photon counters 200A and 200B can be normalized so that readings taken during actual tests of samples can be relied upon as accurate.

Specifically, the tray 100 according to the present invention, once manufactured, is first tested by a reference device to determine a normalized verification value for each photon emitter 102A, 102B, and those verification values are recorded on the tray 100 for each photon emitter 102A, 102B. For example, one of the photon emitters 102A may be determined to emit 12,000 photons in a given time frame whereas the other photon emitter 102B may emit only 11,500 photons in that time frame.

The tray 100 is then sent to a facility for use in connection with that facility's testing machine 104, such as a PRISM® testing machine available from Abbott Laboratories, Inc. To use, the tray 100 is periodically run through the testing machine 104, with the recorded verification values of each photon emitter 102A, 102B checked against the readings taken by that machine's photon counters 200A, 200B. During such periodic testing (e.g., once a month or so), the tray 100 is run through the testing machine 104, with readings taken of a plurality of photon counts (e.g., ten counts) for each photon emitter 102A, 102B. Those readings can be evaluated for consistency (e.g., if the standard deviation divided by the mean of the readings for a photon emitter 102A or 102B is greater than 0.1, a problem with the photon counter 200A or 200B used to count photons from the emitter 102A or 102B is indicated).

During such use of the tray 100 for normalizing readings in the photon counters 200A, 200B, it has been found that over time there will be some decay in the quantity of photons emitted, notwithstanding the long half-life of $C_{14}$. However, for the normalization process, it is preferred that the photon counts not vary by more than about 10% of the verification values determined for the photon emitters 102A, 102B during manufacture.

Figure 1:
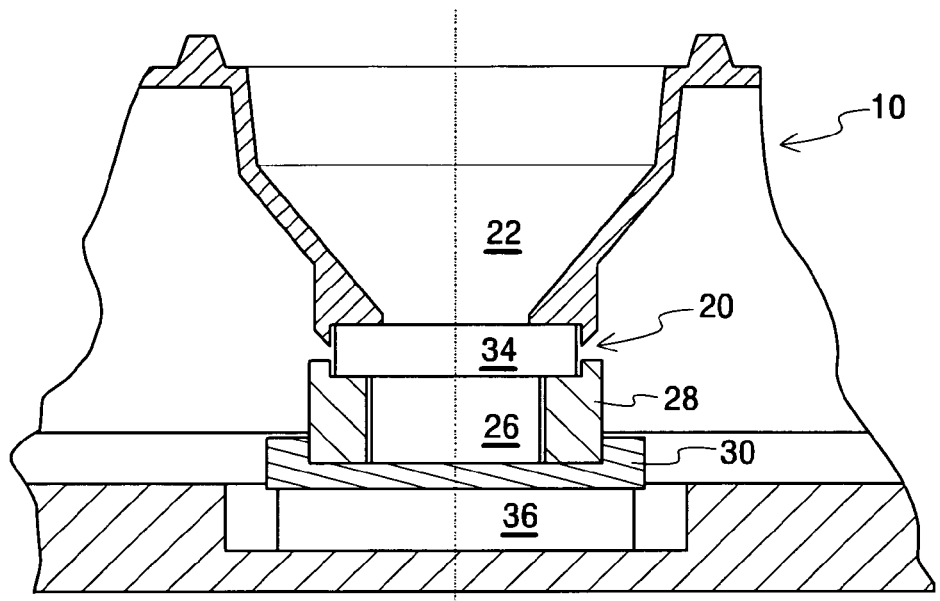
FIG. 1 is a cross sectional view of a well of a normalization tray according to the prior art.
Figure 7:
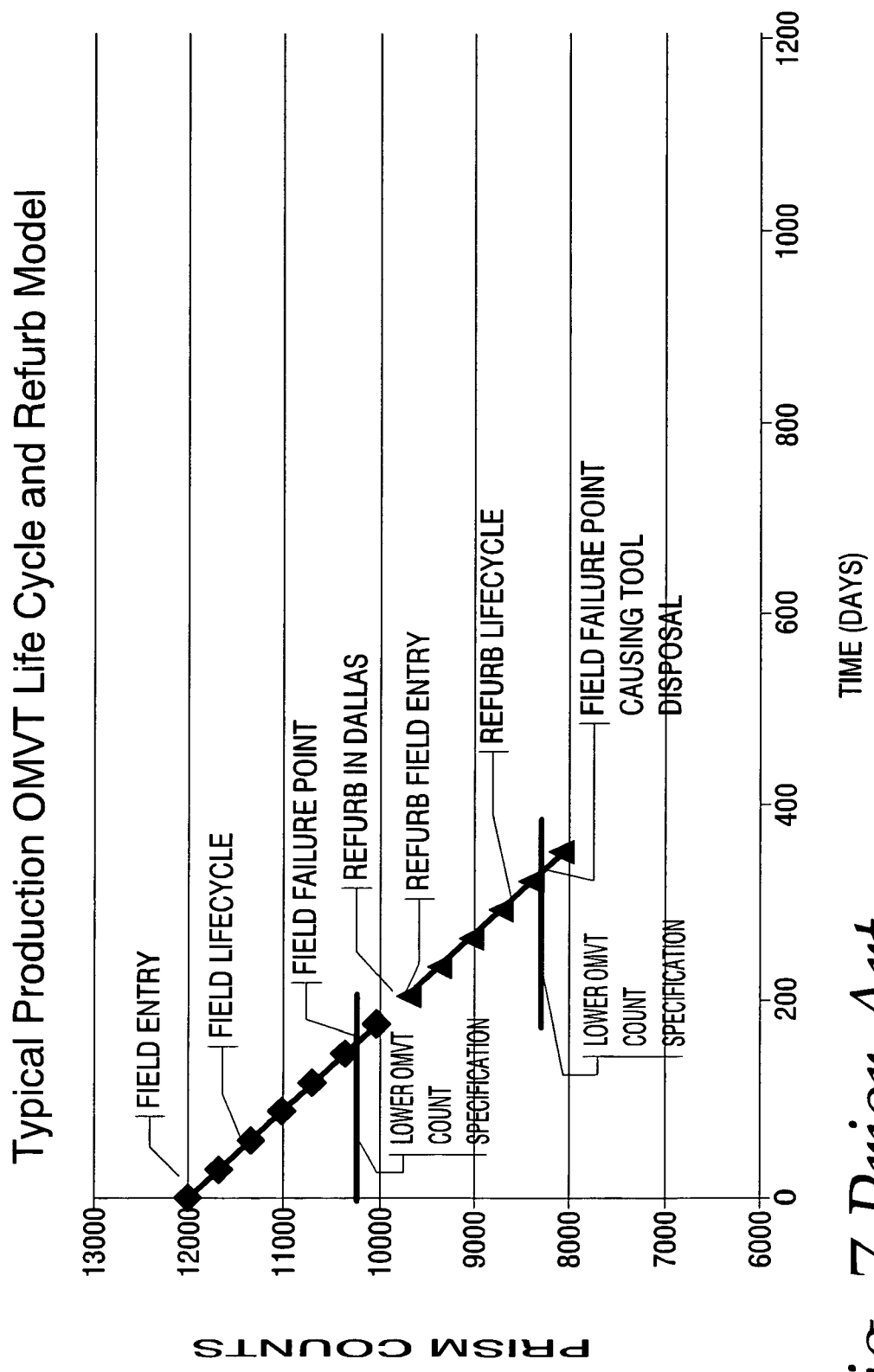
FIG. 7 is a graph illustrating the decay of photon emissions during the useful life of a normalization tray according to the prior art.

However, as illustrated in FIG. 7 for the prior art photon emitter 20 illustrated in FIG. 1, a tray 10 having an emitter with an initial photon count of 12,000 has been found to decay to the point of failure, with unacceptably low photon emissions relative to the initial verification values that it can essentially be considered to fail in less than 200 days. At that point, the tray 10 has heretofore been returned to the manufacturing facility (e.g., in Dallas, Tex. for the PRISM® testing machine, available from Abbott Laboratories) so that new verification values can be determined, although those values are at a much lower value than preferred (e.g., less than 10,000 photons in a given time frame), and will thereafter decay even further. While the tray 10 has then been used thereafter for a while, eventually, the photon count of the refurbished tray 10 will have fallen so low that it can no longer be used. At that point (e.g., about a year in total), the tray 10 is no longer suitable for use and a new tray must be manufactured and shipped to the testing facility to maintain the testing machine 104.

Figure 8:
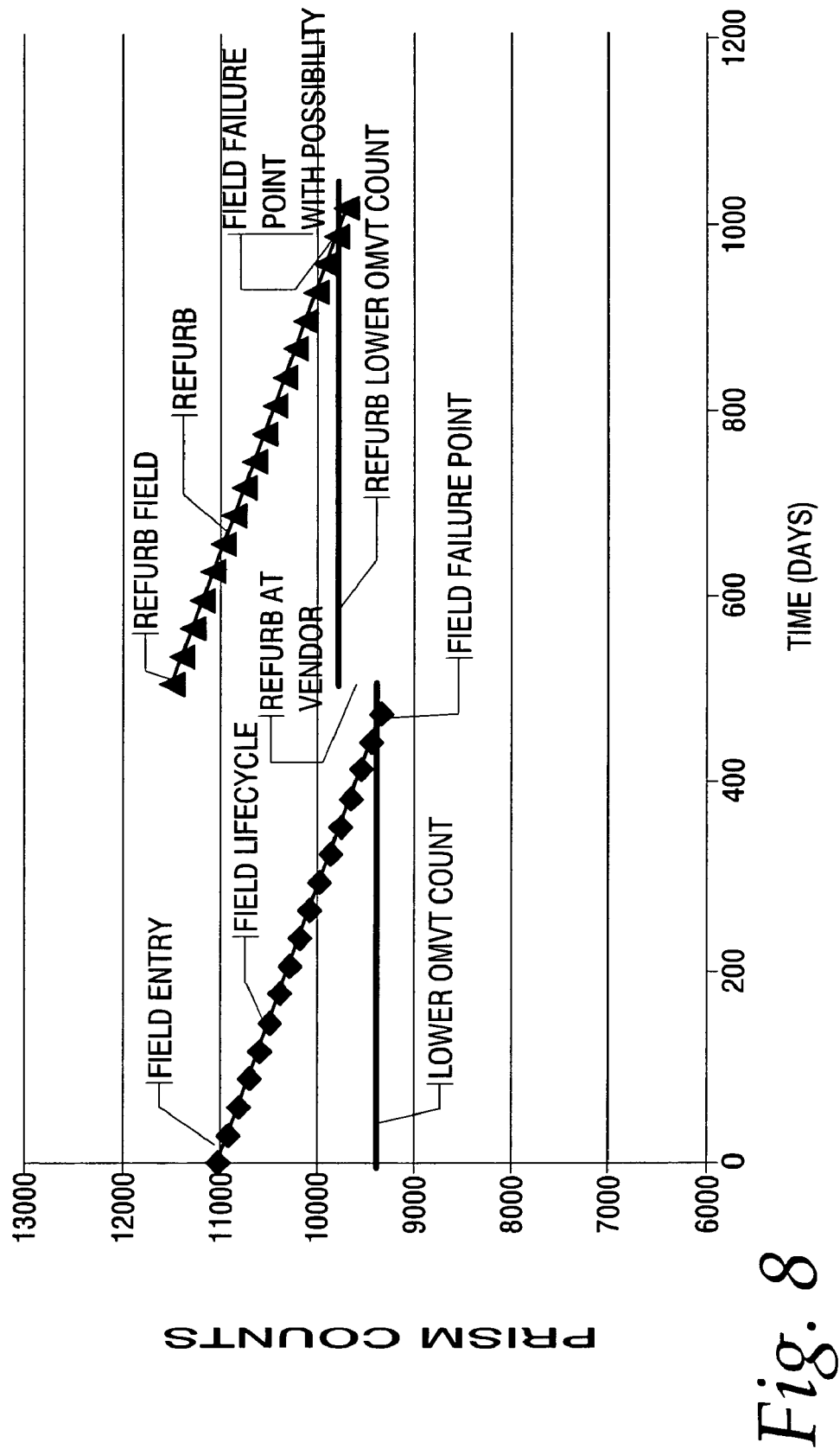
FIG. 8 is a graph illustrating the decay of photon emissions during the useful life of a normalization tray according to the present invention.

By contrast, as illustrated in FIG. 8, the photon emitters 102 of the present invention have been found to decay much more slowly, such that unacceptably low photon emissions are not first encountered for nearly 1½ years (versus less than 200 days with the prior art). At that point, the tray 100 can be shipped back to the manufacturing facility, and the tray can be advantageously refurbished by merely replacing the plastic scintillator disks 146 in the photon emitters 102. In this case, the photon counts of the refurbished photon emitters 102 may actually turn out to be higher than in the original tray 100, and thus not only can the tray 100 be used nearly three times as long (about three years versus one year with the prior art tray 10), but after being refurbished the photon counts will be in the desirable range.

It should thus be appreciated that the normalization tray 100 and photon emitters 102 according to the present invention are modular and portable. They are also customizable for different light spectra by changing the configurations and dimensions of the component parts. Moreover, the radioactive source, the plastic scintillator disk, the neutral density filter, and/or the spacing of components can variously be changed to provide portable stable normalization sources for a wide variety of instrument reader assemblies, photomultiplier tubes, and other photon counting devices. Further, the components of the present invention can be easily manufactured with reliable repeatability.

Still other aspects, objects, and advantages of the present invention can be obtained from a study of the specification, the drawings, and the appended claims. It should be understood, however, that the present invention could be used in alternate forms where less than all of the objects and advantages of the present invention and preferred embodiment as described above would be obtained.

The invention claimed is:

1. An optic module verification device for use in periodic normalization of a testing machine used to test samples in wells of reaction trays, where said testing machine includes X photon counters which each count photons emitted from different tray wells, where X is an integer greater than 1, said verification device comprising:
    a verification tray defining at least X verification wells, said verification wells being located so as to each be associated with a different one of said photon counters when used in the testing machine;
    a photon emitter in each verification well, each photon emitter comprising
        a $C_{14}$ source,
        a scintillator adjacent said $C_{14}$ source, and
        a filter over said scintillator;
    wherein said photon emitters each have a determined initial base value for emitted photons, and each photon emitter is positioned in its verification well to emit photons through said filter to the associated photon counter when used in the testing machine.

2. The verification device of claim 1, wherein said filter is a neutral density glass filter.

3. The verification device of claim 1, wherein said scintillator is plastic with opposite generally flat surfaces.

4. The verification device of claim 3, wherein one scintillator surface is roughened to minimize internal reflectivity.

5. The verification device of claim 1, wherein said verification device includes an open bottom tray in each of the verification wells, and said photon emitters are disposed beneath the tray bottom with said filter adjacent the bottom opening.

6. The verification device of claim 5, further comprising:
    a capsule removably securable to a cap to define a space therebetween enclosing said photon emitter, said capsule including a shoulder surrounding an opening against which said photon emitter filter is secured; and
    a spring between said cap and said $C_{14}$ source, said spring biasing said $C_{14}$ source and said scintillator against said filter.

7. The verification device of claim 6, wherein said capsule shoulder is aligned with said tray bottom opening.

8. The verification device of claim 1, further comprising additional wells in said verification device which are closed to prevent emission of photons, said additional wells each being positioned to be associated with one of the photon counters.

9. The verification device of claim 1, wherein said testing machine is adapted to count photons of a selected light wavelength based on designed wet chemistry of a test specimen, and said scintillator mimics said selected light wavelength.

10. The verification device of claim 1 wherein said $C_{14}$ source comprises a steel disk having a surface adjacent said scintillator coated with $C_{14}$ having about five (5) micro-curies of activity.

11. The verification device of claim 10, further comprising a mylar coating over said $C_{14}$ coating on said steel disk surface.

12. A method of periodically normalizing two photon counters of a testing machine used to test samples in wells of reaction trays by counting photon emitted from reaction trays, comprising the steps of:

(a) providing a verification device having two photon emitters, each photon emitter including a $C_{14}$ source, a scintillator adjacent said $C_{14}$ source, and a filter over said scintillator;

(b) determining normalized reference values for each photon emitter;

(c) counting photons emitted from said verification device photon emitters, wherein one of the photon counters counts the photons emitted from one of the photon emitters and the other photon counter counts the photons emitted from the other photon emitter;

(d) determining normalization values for the photon counters based on said normalized reference values and the photons from said photon emitters counted by said photon counters;

(e) testing samples in reaction tray wells by counting photons using said two photon counters;

(f) normalizing the values of photons counted from said samples using said normalization values;

(g) repeating steps (e) and (f) to test a plurality of reaction trays having wells with samples therein; and (h) periodically repeating steps (c) and (d); and
when the counted photons in step (c) fall below a predetermined value, updating said verification device by replacing the scintillator of each photon emitter, and repeating steps (b) to (h).

13. The method of claim 12, wherein said scintillators are chosen so that said photon emitters each have an initial reference value for emitted photons as determined in step (b) within a selected range, with said predetermined value being the lower end of said selected range.

* * * * *